United States Patent [19]

Kawamata et al.

[11] 4,375,566

[45] Mar. 1, 1983

[54] PROCESS FOR PRODUCING ORTHO-ALKYLATED PHENOLS FROM ANISOLES

[75] Inventors: Motoo Kawamata; Kazushi Ohshima; Mitsuo Onofusa; Akihide Kudoh; Makoto Kotani, all of Yokohama; Takeshi Tsuda, Samukawamachi, all of Japan

[73] Assignee: Mitsui Toatsu Chemicals, Inc., Tokyo, Japan

[21] Appl. No.: 264,391

[22] Filed: May 18, 1981

[30] Foreign Application Priority Data

Nov. 14, 1978 [JP] Japan ................................ 53/139311

[51] Int. Cl.³ .................... C07C 37/055; C07C 39/06
[52] U.S. Cl. ..................................... 568/716; 568/806
[58] Field of Search ................ 568/907, 716, 804, 806

[56] References Cited

U.S. PATENT DOCUMENTS 2,289,886  7/1942  Schmerling ........................ 568/716

Primary Examiner—Werren B. Lone
Attorney, Agent, or Firm—Fisher, Christen & Sabol

[57] ABSTRACT

A process for producing selectively o-alkylated phenols wherein an anisole having at least one ortho positioned hydrogen atom is contacted with a mixed oxide catalyst in the vapor phase.

12 Claims, No Drawings

PROCESS FOR PRODUCING ORTHO-ALKYLATED PHENOLS FROM ANISOLES

BACKGROUND OF THE INVENTION (1) Field of the Invention:

This invention relates to an improved process for producing o-alkylated phenols from anisoles.

(2) Description of the Prior Art:

A number of studies have been made on the process for the production of o-alkylated phenols, particularly 2,6-dimethyl phenol, which is used as the starting material for the production of polyphenylene oxides as useful plastics.

A number of processes for synthesizing o-alkylated phenols by the gaseous phase catalytic reaction of a phenol and an alcohol as the starting material on various kinds of metallic oxides have been known, and there are processes for the synthesis thereof on an industrial scale including a process in which aluminium oxide is used, a process in which magnesium oxide is used as the metallic oxide catalyst respectively, and the like.

Studies have been made on the reaction mechanism for the synthesis of 2,6-xylenol from phenol and methanol by the use of magnesium oxide as the catalyst with the result that (i) no anisole can be formed as an intermediate reaction product, that is, neither o-cresol nor 2,6-xylenol are formed therefrom via an anisole as an intermediate, that (ii) when anisole is solely used as the starting material, a thermal decomposition takes place in the neighborhood of 500° C. to form mainly phenol and benzene, and that (iii) even when anisole and methanol are used as the starting material for reaction, the reaction proceeds to a low extent at 500° C. or lower.

During the production of o-alkylated phenols from phenols and alcohols as the starting material, various kinds of compounds are formed as by-products, and these by-products should be effectively utilized. It is an important problem to be solved to effectively convert anisoles as one of the by-products to o-alkylated phenols to be utilized.

SUMMARY OF THE INVENTION

It is an object of this invention to provide a process for producing o-alkylated phenols at a high selectivity from anisoles which are easy to handle and less corrosive.

It is another object of this invention to provide a process for producing o-alkylated phenols which is capable of utilizing effectively anisoles as the by-product in the production of o-alkylated phenols from phenols and alcohols.

The above objects can be attained by contacting an anisole with a mixed oxide catalyst in the vapor phase to convert the anisole into an o-alkylated phenol.

DETAILED DESCRIPTION OF THE INVENTION

The anisoles used in the process of the present invention are those having a hydrogen atom on at least one of the ortho-positions and are represented by the general formula (1):

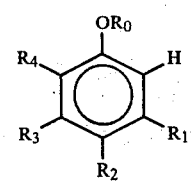

where $R_0$ represents alkyl radicals of 1 to 4 carbon atoms, and $R_1$, $R_2$, $R_3$ and $R_4$ represent independently from each other hydrogen atom, alkyl radicals of 1 to 4 carbon atoms, or unsubstituted or substituted phenyl or naphthyl radicals. Specific examples of the aforesaid anisoles include anisole; o-, m-, p-monomethyl anisoles, monoethyl anisoles, mono-n- or mono-iso-propyl anisoles, mono-n-, mono-iso, or mono-tert-butyl anisols; 2,3-, 2,4-, 2,5-, 3,4- or 3,5-dimethyl anisoles, diethyl anisoles; di-n- or di-iso-propyl anisoles; di-n-, di-iso-, or di-tert-butyl anisoles; trialkyl anisoles, tetralkyl anisoles, phenyl anisoles, naphtyl anisoles, phenetols obtained by replacing metheyl radical of anisole with ethyl radical, other alkoxyl derivatives thereof; and anisoles, phenetols and other alkoxyl derivatives having more than one different functional groups substituted on the aromatic ring. The aforesaid anisoles are preferred to be compounds of anisoles and compounds of phenetols.

The alkylation reaction according to the process of the present invention can be performed by using solely anisoles as the starting material without using alcohols. However the concurrent use of alcohols is preferable in that the proportion of o-alkylated product is increased.

The alcohols used in the present invention are lower saturated aliphatic alcohols of 1 to 4 carbon atoms including methanol, ethanol, n-propanol, iso-propanol, n-butanol, iso-butanol, and tert-butanol.

The formation of o-alkylated phenol according to the present invention is shown as follows:

I. In the case where anisoles are used solely as the starting material:

I-(a) In the case where one hydrogen atom is present on one of the ortho-positions:

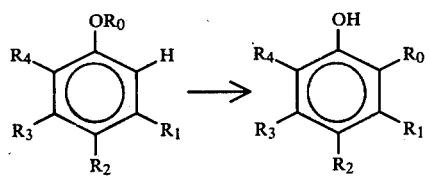

I-(b) In the case where two hydrogen atoms are present on the ortho-positions:

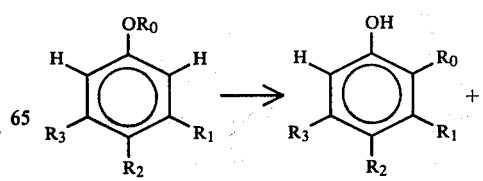

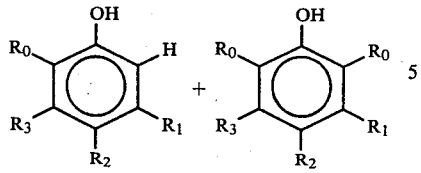
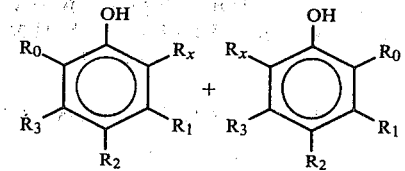

II. In the case where anisoles and alcohols ($R_xOH$) are concurrently used:

II-(a) In the case where one hydrogen atom is present on one of the ortho-positions:

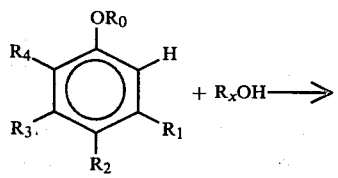

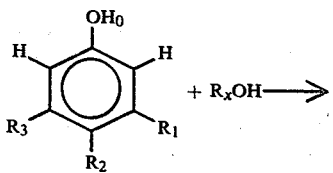

II-(b) In the case where two hydrogen atoms are present on the ortho-positions:

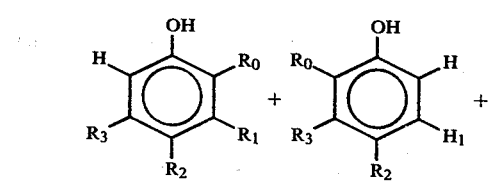

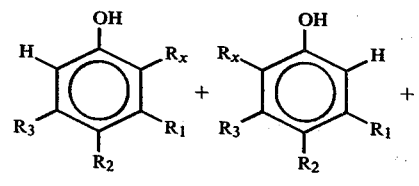

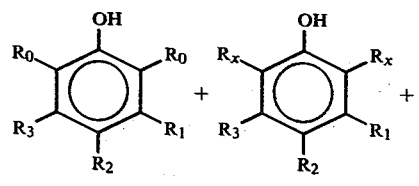

where $R_0$ represents alkyl radicals of 1 to 4 carbon atoms, and $R_1$, $R_2$, $R_3$, and $R_4$ represent independently from each other hydrogen atom, alkyl radicals of 1 to 4 carbon atoms, or unsubstituted or substituted phenyl or naphthyl radicals.

When the alkyl radical $R_x$ of the alcohol used in the aforesaid case II is equal to $R_0$, only the o-alkylated phenols having a single alkyl radical are formed. On the other hand, when $R_x$ is different from $R_0$, various kinds of mixed o-alkylated phenols having alkyl radical $R_x$ and $R_0$ are formed. Therefore it is generally practical to use an alcohol having the same alkyl radical as $R_0$.

Examples of the effective catalysts used in the present invention include a chromium oxide containing catalyst, manganese oxide containing catalyst, iron oxide containing catalyst, magnesium oxide containing catalyst, and the like.

(1) The chromium oxide containing catalyst contains chromium oxide as the major component and, as the minor component, at least one member selected from tin oxide, iron oxide, manganese oxide, aluminium oxide, silicon oxide, boron oxide, alkali metal oxide, alkaline earth metal oxide, and sulfate group, that is, it includes those containing two components such as chromium oxide-tin oxide, chromium oxide-silicon oxide, chromium oxide-boron oxide, chromium oxide-iron oxide, and the like; those containing three components such as chromium oxide-tin oxide-iron oxide, chromium oxide-tin oxide-manganese oxide, and the like; or those containing alkali metal oxide, alkaline earth metal oxide and/or sulfate group in addition thereto.

The aforesaid catalyst has such a composition that the atomic ratio of chromium to other metals in the minor metallic components is preferably in the range of from 100:0.1 to 100:100, and more preferably 100:0.5 to 100:60, and that of chromium to sulfur in the sulfate group is preferably in the range of from 100:0.25 to 100:20, and more preferably 100:0.5 to 100:10.

(2) The manganese oxide containing catalyst contains manganese oxide as the major component, and, as the minor component, at least one member selected from silicon oxide, alkali metal oxide, alkaline earth metal oxide, and sulfate group. For example, it includes manganese oxide-silicon oxide, manganese oxide-silicon oxide-alkali metal oxide and/or alkaline earth metal oxide, manganese oxide-sulfate group, and the like.

The aforesaid catalyst has such a composition that the atomic ratio of manganese to other metals in the minor metallic components is preferably in the range of from 100:0.1 to 100:30, and more preferably 100:0.2 to 100:20, and that of manganese to sulfur in the sulfate group is preferably in the range of from 100:0.01 to 100:20, and more preferably 100:0.05 to 100:15.

(3) The iron oxide containing catalyst contains iron oxide as the major component, and, as the minor component, at least one member selected from silicon oxide, chromium oxide, zinc oxide, manganese oxide, vanadium oxide, alkali metal oxide, and alkaline earth metal oxide. For example, it includes those containing two components such as iron oxide-silicon oxide, iron oxide-chromium oxide, iron oxide-zinc oxide, iron oxide-vanadium oxide, and the like; those containing three components such as iron oxide-silicon oxide-chromium oxide, iron oxide-zinc oxide-chromium oxide, iron oxide-zinc oxide-manganese oxide, iron oxide-silicon oxide-vanadium oxide, and the like; or those containing alkali metal oxide and/or alkaline earth metal oxide in addition thereto.

The aforesaid catalyst has such a composition that the atomic ratio of iron to other metals in the minor metallic components is preferably in the range of from 100:0.05 to 100:100, and more preferably 100:0.1 to 100:60.

(4) The aforesaid magnesium oxide containing catalyst contains magnesium oxide as the major component, and, as the minor component, at least one member selected from tin oxide, copper oxide, lanthanide oxide, actinide oxide, bismuth oxide, and boron oxide. For example, it includes magnesium oxide-tin oxide, magnesium oxide-copper oxide, magnesium oxide-lanthanide oxide and/or actinide oxide, magnesium oxide-bismuth oxide, magnesium oxide-boron oxide, and the like.

The aforesaid catalyst has such a composition that the atomic ratio of magnesium to other metals in the minor metallic components is preferably in the range of from 100:0.5 to 100:80, and more preferably 100:1 to 100:50.

The starting materials for preparing the mixed oxide catalysts used in the present invention include, for example, generally available oxides, hydroxides, halides, nitrates, sulfates, carbonates, organic acid salts, and the like of respective metals. The addition of sulfate group can be accomplished either by using the sulfates of various kinds of metals as starting materials, by incorporating sulfuric acid at any suitable stage of the process of preparing the catalyst, or by adding a suitable sulfonic acid to the catalyst being prepared.

These catalysts may be prepared by any of the conventional methods for the making of mixed metal oxide catalysts. For example, starting materials are mixed, a small amount of water is added thereto, and the resulting mixture is blended well in a kneader or mixer. Alternatively, starting materials are dissolved in water, a suitable basic compound is added thereto, and the co-precipitated insoluble products are mixed with an adequate amount of a compound.

The resulting catalyst is usually dried at a temperature below 250° C., mixed with a suitable granulating additive or processing aid such as microcrystallite cellulose, starch, polyvinyl alcohol, or the like, formed into any desired shape by a suitable technique such as extrusion, compression molding, vibration, rolling, or the like, and then calcined to make it ready for use. Alternatively, the resulting catalyst may be directly calcined and crushed to make it ready for use.

In carrying out the process of the present invention, an inert gas such as nitrogen, carbon dioxide, argon, or the like as a diluent for feeding starting materials to the reaction system is preferably used so that the reaction can proceed smoothly. The addition of water to reactants can extend catalyst life and increase yield.

When an anisole and an alcohol are concurrently used as the starting material, the molar ratio of the anisole to the alcohol is preferably in the range of from 1:0.5 to 1:10, and more preferably 1:1 to 1:5.

In the process of the present invention, the reaction temperature is in the range of from 260° to 480° C., and preferably 300° to 480° C. The reaction temperature at such a high temperature as above 480° C. generally not only decreases the selectivity to o-alkylated phenols, but also unfavorably increases the formation of various polymers of the phenol compound, cyclized high boiling compounds, benzene, toluene, and the like. At such low temperatures as below 260° C. conversion is so low that a large amount of unreacted starting materials must be circulated for reuse which is not practical.

The feed rate of the starting materials to the reaction zone is preferably in the range of from 0.1 to 5 $hr^{-1}$ as liquid hourly space velocity (L.H.S.V.). Generally, it is preferred that when the reaction temperature is high, the L.H.S.V. is increased, and when the reaction temperature is low, the L.H.S.V. is decreased. The reaction can be carried out under atmospheric pressure, under high pressure, or under reduced pressure. The reactor may be of the fixed-bed type, fluidized-bed type, or moving-bed type, and the shell-and-tube type reactor is preferable.

The present invention will be explained by the following Examples.

EXAMPLE 1

100 g of chromium nitrate 9-hydrate, 10 g of tin sulfate, 10 g of iron nitrate 9-hydrate and 60 g of urea were dissolved in 2 l of water, and heated on a heater to form precipitate. Thereafter, 5 mg of cesium nitrate was added thereto and left to stand over night. The resulting precipitate was washed with water, filtered, dried at 180° C., and crushed to be screened to particle sizes ranging from 6 to 12 meshes. 12 ml of the catalyst thus obtained was packed in a glass reactor tube, and calcined at 500° C. for 7 hours to be used for reaction.

Anisole as a sole starting material was introduced into the reactor tube having a temperature controlled at 410° C. at a feed rate of 4 g/hr to carry out reaction.

The reaction product was cooled through a water-cooled condenser, and then analyzed by gas chromatography.

After 2 hours' reaction, conversion of anisole was 43.6%, and selectivities to o-cresol and 2,6-xylenol were 4.5% and 18.9% respectively.

EXAMPLE 2

In the similar manner to Example 1, 8 g of manganese nitrate 6-hydrate in place of iron nitrate 9-hydrate was used to prepare a catalyst. Anisole as a sole starting material was introduced into a reactor tube having a temperature controlled at 440° C. at a feed rate of 3.5 g/hr to carry out reaction.

The result showed that after 2 hours' reaction, conversion of anisole was 51.9%, and selectivities to o-cresol and 2,6-xylenol were 10.3% and 21.4% respectively.

EXAMPLE 3

In the similar procedure to Example 1, a mixed starting material of anisole and methanol having a molar ratio of 1:3 was prepared and introduced at a feed rate of 5 g/hr to effect reaction.

After 2 hours' reaction, conversion of anisole was 78.1%, and selectivities to o-cresol and 2,6-xylenol were 6.2% and 69.4% respectively.

EXAMPLE 4

100 g of manganese nitrate 6-hydrate, and 2 g of water-glass No. 3 were dissolved in 2 l of water, and 29% aqueous ammonia solution was added thereto to form a precipitate. The precipitate thus formed was washed with water, filtered, dried at 180° C., and then crushed to screen to particle sizes ranging from 6 to 12 meshes. 12 ml of the catalyst thus obtained was packed in a glass reactor tube, and calcined at 450° C. for 7 hours to be used for reaction.

Anisole as a sole starting material was introduced into the reactor tube having a temperature controlled at 435° C. at a feed rate of 4 g/hr to carry out reaction.

After 2 hours' reaction, conversion of anisole was 39.4%, and selectivities to o-cresol and 2,6-xylenol were 4.3% and 17.2% respectively.

EXAMPLE 5

In a similar procedure to Example 4, 3 g of calcium nitrate was added concurrently with manganese nitrate 6-hydrate and water-glass No. 3 to prepare a catalyst for use in reaction. Anisole as a sole starting material was introduced into a reactor tube having a temperature controlled at 440° C. at a feed rate of 3.5 g/hr to carry out reaction. The result showed that after 2 hours' reaction, conversion of anisole was 36.7%, and selectivities to o-cresol and 2,6-xylenol were 4.9% and 20.3% respectively.

EXAMPLE 6

In a similar procedure to Example 4, a mixed starting material of anisole and methanol having a molar ratio of 1:3 was prepared and introduced at a feed rate of 5 g/hr to carry out reaction.

After 2 hours' reaction, conversion of anisole was 69.9%, and selectivities to o-cresol and 2,6-xylenol were 6.0% and 60.9% respectively.

EXAMPLE 7

100 g of iron nitrate 9-hydrate, 1 g of chromium nitrate 9-hydrate, and 0.5 g of water-glass No. 3 were dissolved in 2 l of water, and 29% aqueous ammonia solution was added thereto to form precipitate. The precipitate thus formed was washed with water, filtered, dried at 180° C., and then crushed to screen to particle sizes ranging from 5 to 12 meshes. 12 ml of the catalyst thus formed was packed in a glass reactor tube, and calcined at 450° C. for 7 hours to be used for reaction.

Anisole as a sole starting material was introduced into the reactor tube having a temperature controlled at 390° C. at a feed rate of 4 g/hr to carry out reaction.

After 2 hours' reaction, conversion of anisole was 44.4%, and selectivities to o-cresol and 2,6-xylenol were 4.1% and 19.5% respectively.

EXAMPLE 8

In a similar procedure to Example 7, a catalyst was prepared without adding chromium nitrate 9-hydrate and used for reaction. Anisole as a sole starting material was introduced into a reactor tube having a temperature controlled at 390° C. at a feed rate of 3.5 g/hr to carry out reaction. The result showed that after 2 hours' reaction, conversion of anisole was 38.6%, and selectivities to o-cresol and 2,6-xylenol were 5.7% and 19.4% respectively.

EXAMPLE 9

In a similar procedure to Example 7, a mixed starting material of anisole and methanol having a molar ratio of 1:3 was prepared and introduced at a feed rate of 5 g/hr to carry out reaction.

After 2 hours' reaction, conversion of anisole was 70.5%, and selectivities to o-cresol and 2,6-xylenol were 6.2% and 61.7% respectively.

EXAMPLE 10

100 g of magnesium nitrate 6-hydrate, and 10 g of stannous chloride 2-hydrate were dissolved in 1 l of water, and 29% aqueous ammonia solution was added thereto to form precipitate. The precipitate thus formed was washed with water, filtered, dried at 180° C., and then crushed to screen to particle sizes ranging from 6 to 12 meshes. 12 ml of the catalyst thus obtained was packed in a glass reactor tube, and calcined at 550° C. for 7 hours to use for reaction.

Anisole as a sole starting material was introduced into the reactor tube having a temperature controlled at 465° C. at a feed rate of 4 g/hr to carry out reaction.

The result showed that after 2 hours' reaction, conversion of anisole was 31.4%, and selectivities to o-cresol and 2,6-xylenol were 6.9% and 12.0% respectively.

EXAMPLE 11

In a similar procedure to Example 10, 5 g of manganese nitrate was added concurrently with magnesium nitrate 6-hydrate and stannous chloride to prepare a catalyst. Anisole as a sole starting material was introduced into a reactor tube having a temperature controlled at 455° C. at a feed rate of 3.5 g/hr to carry out reaction. The result showed that after 2 hours' reaction, conversion of anisole was 40.4%, and selectivities to o-cresol and 2,6-xylenol were 7.0% and 14.1% respectively.

EXAMPLE 12

In a similar procedure to Example 10, a mixed starting material of anisole and methanol having a molar ratio of 1:3 was prepared and introduced at a feed rate of 5 g/hr to carry out reaction.

The result showed that after 2 hours' reaction, conversion of anisole was 65.0%, and selectivities to o-cresol and 2,6-xylenol were 8.4% and 53.3% respectively.

What is claimed is:

1. A process for producing o-alkylated phenols comprising contacting an anisole represented by the formula

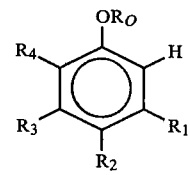

wherein $R_0$ represents alkyl radicals of 1 to 4 carbon atoms, $R_1$ $R_2$, $R_3$, and $R_4$ represent hydrogen atoms, alkyl radicals of 1 to 4 carbon atoms, and may be identical to or different from each other, with a mixed oxide catalyst in the vapor phase at a reaction temperature in the range of from 260° C. to 480° C. to selectively form an o-alkylated phenol, wherein said mixed oxide catalyst is a chromium oxide containing catalyst, a manganese oxide containing catalyst, an iron oxide containing catalyst, or a magnesium oxide containing catalyst; wherein said chromium oxide containing catalyst contains chromium oxide as the major component, and at least one member selected from the group consisting of tin oxide, iron oxide, manganese oxide, aluminium oxide, silicon oxide, boron oxide, alkali metal oxides, alkaline earth metal oxides and the sulfate group; wherein said manganese oxide containing catalyst contains manganese oxide as the major component, and at least one member selected from the group consisting of silicon oxide, alkali metal oxides, alkaline earth metal oxides, and the sulfates group; wherein said iron oxide containing catalyst contains iron oxide as the major component, and at least one member selected from the group consisting of silicon oxide, chromium oxide, zinc oxide, manganese oxide, vanadium oxide, alkali metal oxides, and alkaline earth metal oxides; and wherein said magnesium oxide containing catalyst contains magnesium oxide as the major component, and at least one member selected from the group consisting of tin oxide, copper oxide, lanthanide oxide, actinide oxide, bismuth oxide and boron oxide.

2. A process as claimed in claim 1, wherein said anisole is subjected to a vapor phase catalytic reaction concurrently with a lower saturated aliphatic alcohol of 1 to 4 carbon atoms.

3. A process as claimed in claim 2, wherein the molar ratio of anisole to alcohol is in the range of from 1:0.5 to 1:10.

4. A process as claimed in claim 1, wherein an atomic ratio between said chromium and said tin, iron, manganese, aluminium, silicon, boron, alkali metal, or alkaline earth metal in said catalyst is in the range of from 100:0.1 to 100:100.

5. A process as claimed in claim 1, wherein an atomic ratio of chromium of said chromium oxide to sulfur of said sulfate group in said catalyst is in the range of from 100:0.25 to 100:20.

6. A process as claimed in claim 1, wherein an atomic ratio of said manganese to said silicon, said alkali metal, or said alkaline earth metal in said catalyst is in the range of from 100:0.1 to 100:30.

7. A process as claimed in claim 1, wherein an atomic ratio of manganese of said manganese oxide to sulfur of said sulfate group in said catalyst is in the range of from 100:0.01 to 100:20.

8. A process as claimed in claim 1, wherein an atomic ratio of said iron to said other metallic component in said catalyst is in the range of from 100:0.05 to 100:100.

9. A process as claimed in claim 1, wherein an atomic ratio of said magnesium to said other metallic component is in the range of from 100:0.5 to 100:80.

10. A process as claimed in claim 2 or 1 wherein the reaction is conducted in the presence of an inert gas.

11. A process as claimed in claim 2 or 1 wherein water is added to the reaction system.

12. A process as claimed in claim 2 wherein the alkyl radical of said alcohol is the same alkyl radical as $R_0$.

* * * * *